US 6,705,988 B2

(12) United States Patent
Spence et al.

(10) Patent No.: US 6,705,988 B2
(45) Date of Patent: *Mar. 16, 2004

(54) DEVICE TO PERMIT OFFPUMP BEATING HEART CORONARY BYPASS SURGERY (75) Inventors: Paul A. Spence, Louisville, KY (US); Warren Williamson, IV, Loveland, OH (US)

(73) Assignee: Origin Medsystems, Inc., Santa Clara, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 10/029,792

(22) Filed: Dec. 28, 2001

(65) Prior Publication Data

US 2002/0065451 A1 May 30, 2002

Related U.S. Application Data (63) Continuation of application No. 09/109,924, filed on Jul. 2, 1998, now Pat. No. 6,390,976, which is a continuation-in-part of application No. 09/087,511, filed on May 29, 1998, now Pat. No. 6,338,712, which is a continuation-in-part of application No. 08/936,184, filed on Sep. 17, 1997, now Pat. No. 6,019,722.

(51) Int. Cl.[7] ................................................. A61B 1/32
(52) U.S. Cl. ......................................... 600/201; 600/37
(58) Field of Search ................................. 600/201, 204, 600/205, 206, 208, 210, 214, 227–229, 231, 233, 235, 37

(56) References Cited

U.S. PATENT DOCUMENTS

| 452,131 A | 5/1891 | Haughawout |
| 810,675 A | 1/1906 | Richter |
| 1,706,500 A | 3/1929 | Smith |
| 2,082,782 A | 6/1937 | Allen |
| 2,296,793 A | 9/1942 | Kirschbaum |

(List continued on next page.)

FOREIGN PATENT DOCUMENTS

| DE | 3138589 A1 | 4/1983 |
| DE | 9004513 | 6/1990 |
| DE | 4139695 A1 | 6/1993 |
| EP | 0 293 760 B1 | 12/1988 |
| EP | 0 293 760 A3 | 12/1988 |

(List continued on next page.)

OTHER PUBLICATIONS

C.W. Akins et al., "Preservation of Interventricular Septal Function in Patients Having Coronary Artery Bypass Grafts Without Cardiopulmonary Bypass," American Heart Journal, vol. 107, No. 2 Feb., 1984, pp. 304–309.

(List continued on next page.)

Primary Examiner—Kevin Shaver
Assistant Examiner—Michael B. Priddy
(74) Attorney, Agent, or Firm—Law Office of Alan W. Cannon (57) ABSTRACT A system for manipulating and supporting a beating heart during cardiac surgery, including a gross support element for engaging and supporting the heart (the gross support element preferably including a head which is sized and shaped to cradle the myocardium of the left ventricle"), a suspension head configured to exert lifting force on the heart when positioned near the apical region of the heart at a position at least partially overlying the right ventricle, and a releasable attachment element for releasably attaching at least one of the gross support element and the suspension head to the heart. The releasable attachment element can be a mechanical element (such as one or more staples or sutures') or an adhesive such as glue. Alternatively, the system includes a suspension head and a releasable attachment element for releasably attaching it to the heart, but does not include a gross support element.

9 Claims, 8 Drawing Sheets

U.S. PATENT DOCUMENTS

| | | |
|---|---|---|
| 2,590,527 A | 3/1952 | Fluck |
| 2,693,795 A | 11/1954 | Grieshaber |
| 2,863,444 A | 12/1958 | Winsten |
| 3,361,133 A | 1/1968 | Kimberley et al. |
| 3,392,722 A | 7/1968 | Jorgensen |
| 3,584,822 A | 6/1971 | Oram |
| 3,683,926 A | 8/1972 | Suzuki |
| 3,720,433 A | 3/1973 | Rosfelder |
| 3,783,873 A | 1/1974 | Jocobs |
| 3,807,406 A | 4/1974 | Rafferty et al. |
| 3,858,926 A | 1/1975 | Ottenhues |
| 3,882,855 A | 5/1975 | Shulte et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,052,980 A | 10/1977 | Grams et al. |
| 4,096,864 A | 6/1978 | Kletschka et al. |
| 4,217,890 A | 8/1980 | Owens |
| 4,226,228 A | 10/1980 | Shin et al. |
| 4,230,119 A | 10/1980 | Blum |
| 4,300,564 A | 11/1981 | Furihata |
| 4,306,561 A | 12/1981 | de Medinaceli |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,617,916 A | 10/1986 | Le Vahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,925,443 A | 5/1990 | Heilman et al. |
| 4,949,707 A | 8/1990 | Le Vahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | Le Vahn |
| 5,098,369 A | 3/1992 | Heilman et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Goover |
| RE34,150 E | 12/1992 | Santilli et al. |
| 5,167,223 A | 12/1992 | Koros et al. |
| 5,171,254 A | 12/1992 | Sher |
| 5,196,003 A | 3/1993 | Bilweis |
| 5,231,974 A | 8/1993 | Giglio et al. |
| 5,256,132 A | 10/1993 | Snyders |
| 5,268,640 A | 12/1993 | Du et al. |
| 5,287,861 A | 2/1994 | Wilk |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cochen |
| 5,348,259 A | 9/1994 | Blanco et al. |
| 5,363,882 A | 11/1994 | Chikama |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,453,078 A | 9/1995 | Valentine et al. |
| 5,467,763 A | 11/1995 | McMahon et al. |
| 5,480,425 A | 1/1996 | Ogilive |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,522,819 A | 6/1996 | Graves et al. |
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman et al. |
| 5,571,215 A | 11/1996 | Sterman et al. |
| 5,573,496 A | 11/1996 | McPherson et al. |
| 5,582,580 A | 12/1996 | Buckman, Jr. et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,632,746 A | 5/1997 | Middleman et al. |
| 5,651,378 A | 7/1997 | Metheny et al. |
| 5,662,300 A | 9/1997 | Michelson et al. |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |

| | | |
|---|---|---|
| 5,795,291 A | 8/1998 | Koros et al. |
| 5,797,960 A | 8/1998 | Stevens et al. |
| 5,799,661 A | 9/1998 | Boyd et al. |
| 5,807,243 A | 9/1998 | Vierra et al. |
| 5,813,410 A | 9/1998 | Levin |
| 5,818,231 A | 10/1998 | Smith |
| 5,836,311 A | 11/1998 | Borst et al. |
| 5,864,275 A | 1/1999 | Ohashi et al. |
| 5,865,730 A | 2/1999 | Fox et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A | 5/1999 | Corey et al. |
| 5,906,607 A | 5/1999 | Taylor et al. |
| 5,908,378 A | 6/1999 | Kovacs et al. |
| 5,921,979 A | 7/1999 | Kovac et al. |
| 5,927,284 A | 7/1999 | Borst et al. |
| 5,947,896 A | 9/1999 | Sherts et al. |
| 5,957,835 A | 9/1999 | Anderson et al. |
| 5,967,973 A | 10/1999 | Sherts et al. |
| 5,976,069 A | 11/1999 | Navia et al. |
| 5,984,864 A | 11/1999 | Fox et al. |
| 6,013,027 A | 1/2000 | Khan et al. |
| 6,015,378 A * | 1/2000 | Borst et al. .................... 600/37 |
| 6,015,427 A | 1/2000 | Mueller et al. |
| 6,019,722 A | 2/2000 | Spence et al. |
| 6,032,672 A | 3/2000 | Taylor |
| 6,033,362 A | 3/2000 | Cohn |
| 6,036,641 A | 3/2000 | Taylor et al. |
| 6,159,201 A * | 12/2000 | Hamilton et al. .............. 606/1 |
| 6,328,688 B1 | 12/2001 | Borst et al. |
| 6,334,843 B1 | 1/2002 | Borst et al. |
| 6,336,898 B1 | 1/2002 | Borst et al. |
| 6,338,712 B2 | 1/2002 | Spence et al. |
| 6,361,493 B1 | 3/2002 | Spence et al. |
| 6,364,826 B1 | 4/2002 | Borst et al. |
| 6,371,906 B1 | 4/2002 | Borst et al. |
| 6,390,976 B1 * | 5/2002 | Spence et al. .............. 600/210 |
| 6,394,948 B1 | 5/2002 | Borst et al. |
| 2002/0161285 A1 * | 10/2002 | Spence et al. .............. 600/210 |

FOREIGN PATENT DOCUMENTS

| | | |
|---|---|---|
| EP | 0 293 760 A2 | 12/1988 |
| EP | 0 630 629 A1 | 5/1994 |
| EP | 668 058 A1 | 2/1995 |
| EP | 0 791 330 A2 | 2/1997 |
| EP | 0 820 721 A1 | 7/1997 |
| EP | 0 791 329 A1 | 8/1997 |
| EP | 0 808 606 A1 | 11/1997 |
| EP | 0 820 721 A1 | 1/1998 |
| EP | 0 919 193 A1 | 2/1999 |
| GB | 168216 | 9/1921 |
| GB | 2 233 561 A | 1/1991 |
| GB | 2 267 827 A | 12/1993 |
| SU | 938967 | 7/1982 |
| WO | WO 87/04081 | 7/1987 |
| WO | WO 88/00481 | 1/1988 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 96/40354 | 12/1996 |
| WO | WO 97/10753 | 3/1997 |
| WO | WO 97/26828 A | 7/1997 |
| WO | WO 97/40752 | 11/1997 |
| WO | WO 98/37814 | 9/1998 |
| WO | WO 98/49944 | 11/1998 |
| WO | WO 99/60929 | 12/1999 |
| WO | WO 99/60930 | 12/1999 |
| WO | WO 00/10466 | 3/2000 |
| WO | WO 01/58362 A1 | 8/2001 |

OTHER PUBLICATIONS

Ancalmo, N. and J. L. Ochsner: "A Modified Sternal Retractor," Ann. Thorac, Surg. 21 (1976) 174.

Angelini, G.D., M.D. et al., "A Fiber–Optic Retractor for Harvesting the Internal Mammary Artery," Ann. Thorac. Surg. (1990; 50:314–5).

Angelini, G.D., M.D., "A Simple, Inexpensive Method of Heart Retraction During Coronary Artery Bypass Surgery," Ann. Thora. Surg 46:46–247, Aug. 1988.

Anstadt, M.P. MD et al., "Direct Mechanical Ventricular Actuation for Cardiac Arrest in Humans," Chest, vol. 100, No. 1, Jul. 1991, pp. 86–92.

Antinori, C. et al., "A Method of Retraction During Reoperative Coronary Operations Using the Favaloro Retractor," The Society of Thoracic Surgeons: 1989.

Archer, R. DO et al., "Coronary Artery Revascularization Without Cardiopulmonary Bypass," Texas Heart Institute Journal, vol. 11, No. 1, Mar. 1984, pp. 52–57.

Arom, K.V., et al., "Mini–Sternotomy for Coronary Artery Bypass Grafting," The Annals of Thoracic Surgery 1996; 61:1271–2.

Ballantyne, C.M. et al. "Delayed Recovery for Severely 'Stunned' Myocardium With the Support of a Left Ventricular Assist Device after Coronary Artery Bypass Graft Surgery," Journal of the American College of Cardiology, vol. 10, No. 3, Sep. 1987, pp. 710–712.

Bedellino, M.M., et al., "The Cardiac Rag—Simple Exposure of the Heart," Texas Heart Institute Journal, vol. 15, No. 2, 1988, 134–35.

Beg, R.A. et al., "Internal Mammary Retractor," Ann Thorac, Surg., vol. 39, No. 1, Jan. 1985, pp. 286–287.

Benetti, F. J. et al., "Direct Coronary Surgery with Saphenous Vein Bypass Without Either Cardiopulmonary Bypass Graft or Cardiac Arrest," The Journal of Cardiovascular Surgery, vol. 26, No. 3, May–Jun., 1985, pp. 217–222.

Benetti, F. J. et al., "Direct Myocardial Revascularization Without Extracorporeal Circulation," Chest, vol. 100, No. 2, Aug., 1991, pp. 312–316.

Benetti, F. J., "Coronary Revascularization with Arterial Conduits via a Small Thoracotomy and Assisted by Thoracoscopy, Although Without Cardiopulmonary Bypass," Cor Europaeum 4 (1) 22–24 (1995).

Borst et al., "Coronary Artery Bypass Grafting Without Cardiopulmonary Bypass and Without Interruption of Native Coronary Flow Using a Novel Anastomosis Site Restraining Device ('Octopus')", JAAC vol. 27, No. 6, May 1996:1356–64.

C. Borst et al., entitled "Regional Cardiac Wall Immunobilization for Open Chest and Closed Chest Coronary Artery Bypass Grafting on the Beating Heart: The 'Octopus' Method," Circulation, (Oct. 15, 1995) vol. 92, No. 8 supplemental I,I–177.

Bugge, M., "A New Internal Mammary Artery Retractor," Thorac. Cardiovasc Surgeon 38, pp. 316–317 (1990).

Buffolo, E., et al., "Direct Myocardial Revascularization Without Cardiopulmonary Bypass," Thorac. Cardiovasc. Surgeon, 33 (1985) pp. 26–29.

Calafiore, A. M., et al., "Minimally Invasive Coronary Artery Bypass Grafting," The Annals of Thoracic Surgery, 62:1545–8, 1996.

Calvin, I. F. & Newman, D.C., "Circumflex Exposure Using a Cardiac Sling," Ann Thorac Surg 1990:49:833–4.

Campalani, G., M.D., et al., "A New Self–Retaining Internal Mammary Artery Retractor," J. Cardiovas. Surg. 28, 1987, pp. 347–348.

Chaux, A. and Blanche, C., "A New Concept in Sternal Retraction: Applications for Internal Mammary Artery Dissection and Valve Replacement Surgery," Ann. Thorac. Surg. 42, Oct. 1986, pp. 473–474.

Cohen, A.S., et al., "Mini–Sternotomy for Coronary Artery Bypass Grafting," The Annals for Thoracic Surgery 1996; 62:1884–85.

Cutler, B.S. and Cantelmo, N.L., "New Use for an Old Clamp," Archives of Surgery—vol. 115, 1136–37, Sep. 1980.

Delacroix–Chevalier Surgical Instruments, IMA Saving Packages Brochure.

DelRossi, AJ and Lemole, GM, "A New Retractor to Aid in Coronary Artery Surgery," The Annals of Thoracic Surgery, vol. 36, No. 1, 101–102, Jul. 1983.

English abstract for Russian Patent No. SU 938967.

Fanning, W. J. et al., "Reoperative Coronary Artery Bypass Grafting Without Cardiopulmonary Bypass," The Annals of Thoracic Surgery, vol. 55, No. 2, Feb. 1993, pp. 486–489.

Favaloro, R. G., et al. "Direct Myocardial Revascularization by Saphenous Vein Graft," The Annals of Thoracic Surgery, vol. 10, No. 2, Aug. 1970, pp. 97–111.

Fonger, J. D., et al., "Enhanced Preservation of Acutely Ischmenic Myocardium with Transeptal Left Ventricular Assist," The Annals of Thoracic Surgery, vol. 57, No. 3, Mar., 1994, pp. 570–575.

Gacioch, G. M., MD, et al., "Cardiogenic Shock Complicating Acute Myocardial Infarction: The Use of Coronary Angioplasty and the Integration of the New Support Device into Patient Management," Journal of the American College of Cardiology, vol. 19, No. 3, Mar. 1, 1992.

Green, GE., "Technique of Internal Mammary–Coronary Artery Anastomosis," The Journal of Cardiovascular Surgery, 78:455–79, 1979.

Grundeman et al., "Vertical Displacement of the Beating Heart by the Octopus Tissue Stabilizer: Influence on Coronary Flow", Ann Thorac Surg 1998; 65: 138–152.

Grundeman et al., "Hemodynamic Changes During Displacement of the Beating Heart by the Utrecht Octopus Method", Ann Thorac Surg 1997; 66:576–579.

Guzman, F. M.D., "Transient Radial Nerve Injury Related to the Use of A Self Retraining Retractor for Internal Mammary Artery Dissection," J. Cardiovasc. Surg. 30, 1989, pp. 1015–1016.

Hasan, R. I., et al., "Technique of Dissecting the Internal Mammary After Using The Moussalli Bar," European Journal of Cardio Thoracic Surgery, 4:571–572, 1990.

Itoh, Toshiaki, M.D., et al., "New Modification of a Mammary Artery Retractor," Ann. Thorac. Surg. 9, 1994; 57:1670–1.

Jansen et al., "Experimental Off–Pump Grafting of a Circumflex Brach via Sternotomy Using a Suction Device", Ann Thorac Surg 1997; 63:S93–6.

Jansen et al., "Off–Pump Coronary Bypass Grafting: How to Use the Octopus Tissue Stabilizer," Ann Thorac Surg 1998; 66:576–9.

Japanese Journal of Thoracic Surgery, vol. 42, No. 2, 1989. Japanese Article "Heart Retractor".

Janke, W. H., "Heart Support for Coronary Bypass Surgery Involving the Circumflex Artery System," The Journal of Thoracic and Cardiovascular Surgery, pp. 883–884.

Kolessov, V.I., M.D., "Mammary Artery–Coronary Artery Anastomosis as Method of Treatment for Angina Pectoris," Thoracic and Cardiovascular Surgery, vol. 54, No. 4, Oct. 1967, pp. 535–544.

Kazama, S. et al., "Fabric Heart Retractor for Coronary Artery Bypass Operations," The Annals of Thoracic Surgery, 55:1582–3, 1993.

Kresh, J. Y., et al., "Heart–Mechanical Assist Device Interaction," Trans. Am. Soc. Artif. Intern. Organs, vol. XXXII, 1986, pp. 437–443.

Lavergne, et al., "Transcatheter Radiofrequency Ablation of Atrial Tissue Using a Suction Catheter," PACE, vol. 12, Jan. 1989, Part II, pp. 177–186.

Lonn, U., M.D., et al., "Coronary Artery Operation Supported by the Hemopump: An Experimental Study on Pigs," The Annals of Thoracic Surgery, vol. 58, No. 1, Jul., 1994, pp. 516–523.

Matsuura, A., et al., "A New Device for Exposing the Circumflex Coronary Artery," The Annals of Thoracic Surgery, 59:1249–50, 1995, pp. 1249–1250.

McGee, M. G.,et al., "Extended Clinical Support with an Implantable Left Ventricular Assist Device," Trans. Am. Soc. Artif. Intern. Organs, vol. XXXV, 1989, pp. 614–616.

McKeown, P.P. et al., "A Modified Sternal Retractor for Exposure of the Internal Mammary Artery," Ann. Thorac. Surg. 32 (1981) 619.

Ochsner, J. L., et al., "Surgical Management of Diseased Intracavitary Coronary Arteries," The Annals of Thoracic Surgery, vol. 38, No. 4, Jul., pp. 356–362, Oct. 1984.

Parsonnet, V. MD, et al., "Graduated probes for Coronary Bypass Surgery," The Journal of Thoracic and Cardiovascular Surgery, vol. 68, No. 3, 424–26 (Sep. 1974).

Parsonnet, V. MD, et al., "Self–Retaining Epicardial Retractor for Aortocoronary Bypass Surgery," The Journal of Thoracic and Cardiovascular Surgery, 629–30 1979.

Pfister, A. J. M.D., et al., "Coronary Artery Bypass Without Cardiopulmonary Bypass," The Annals of Thoracic Surgery, vol. 54, No. 6, Dec. 1992, pp. 1085–1092.

Phillips, Steven J., M.D. et al., "A Versatile Retractor for Use in Harvesting the Internal Mammary Artery and Performing Standard Cardiac Operations," J. Thorac. Cardiovasc. Surg. (1989; 97:633–5).

Pilling Surgical Instruments, A Rusch International Company Brochure.

Pittman, John, M.D., et al., "Improved Visualization of the Internal Mammary Artery with a New Retractor System," Ann. Thorac. Surg., 1989; 48:869–70.

Riahi, M.,et al., "A Simple Technique and Device to Provide a Bloodless Operative Field in Coronary Artery Surgery Without Cross–Clamping the Aorta," The Journal of Thoracic and Cardiovascular Surgery, vol. 66, No. 6, Dec. 1973, pp. 974–978.

Richenbacher, W. E., MD, et al., "Current Status of Cardiac Surgery: A 40–Year Review," Journal of American College of Cardiology, vol. 14, No. 3, pp. 535–544.

Robicsek, F., "Aortic Spoon–Jaw Clamp for Aorto–Saphenous Vein Anastomosis," J. Card. Surg., 1995; 10:583–585.

Robinson, M. C., et al., "A Minimally Invasive Surgical Method for Coronary Revascularization—Preliminary Experience in Five Patients," Circulation, Oct. 15, 1995, vol. 92, No. 8, 1–176.

Rousou, J. et al., "Cardiac Retractor for Coronary Bypass Operations," Ann Thorac. Surg, 1991; 52:877–8.

Roux, D., M.D. et al., "Internal Mammary Artery Dissection: A Three Dimensional Sternal Retractor," J. Cardiovasc. Surg., 1989; 30:996–7.

Roux, D., M.D. et al., "New Helper Instrument in Cardiac Surgery," Ann. Thorac. Surg., 1989, 48:595–596.

Ruzevich, S. A., et al., "Long–Term Follow–Up of Survivors of Postcardiotomy Circulatory Support," Trans. Am. Soc. Artif. Intern. Organs, vol. XXXIV, 1988, pp. 116–124.

Scholz, K. H., et al., "Transfemoral Placement of the Left Ventricular Assist Device 'Hemopump' During Mechanical Resuscitation," Thoracic and Cardiovascular Surgeon, vol. 38 (1990) pp. 69–72.

Splittgerber et al., "Exposing the Circumflex Coronary Artery: The Heartflip Technique," Ann Thorac Surg. 1996;61:1019–20.

Stevens, et al., "Closed Chest Coronary Artery Bypass With Cardioplegic Arrest in the Dog," 67th Scientific Session, 238, I–251.

Takahashi et al.,"A New Instrument for Immobilization and Hemostasis During Minimally Invasive Direct Coronary Artery Bypass ('MIDCAB doughnut'): Experimental Study", J Card Surg 1997; 12:185–189.

Trapp, et al., "Placement of Coronary Artery Bypass Graft without Pump Oxygenator," Journal of the Society of Thoracic Surgeons and The Southern Thoracic Surgeons Assn. vol. 19, No. 1, Jan. 1975.

Trapp W.G., "To Use or Not To Use the Pump Oxygenator in Coronary Bypass Operations," The Annals of Thoracic Surgery, vol. 19, No. 1, Jan., 1975, pp. 108–109.

USSC Cardiovascular Thora–Lift™, United States Surgical Corporation, Norwalk, Connecticut, Product Brochure.

Vincent, J.G., "A Compact Single Post Internal Mammary Artery Dissection Retractor," Eur. J. Cardio–Thor. Surg. 3 (1989) 276–277.

Westaby, S., "Coronary Surgery Without Cardiopulmonary Bypass," British Heart Journal Vol 73 pp. 203–205, 1995.

Westaby, S. et al. "Less Invasive Coronary Surgery: Consensus From the Oxford Meeting," The Annals of Thoracic Surgery, 62:924–31, 1996.

Zumbro, G. L. et al., "A Prospective Evaluation of the Pulsatile Assist Device," The Annals of Thoracic Surgery, vol. 28, No. 2, Aug. 1979, pp. 269–273.

* cited by examiner

DEVICE TO PERMIT OFFPUMP BEATING HEART CORONARY BYPASS SURGERY

CROSS REFERENCE TO RELATED APPLICATIONS

The present application is a continuation of U.S. patent application Ser. No. 09/109,924 filed on Jul. 2, 1998, now U.S. Pat. No. 6,390,976, which is a continuation-in-part application of U.S. patent application Ser. No. 09/087,511 filed on May 29, 1998, now U.S. Pat. No. 6,338,712, which is a continuation-in-part of U.S. patent application Ser. No. 08/936,184 filed on Sep. 17, 1997, now U.S. Pat. No. 6,019,722.

TECHNICAL FIELD OF THE INVENTION

The present invention relates to the general art of cardiac surgery, and to the particular field of heart retractors used in beating heart surgery.

BACKGROUND OF THE INVENTION

There are as many as 300,000 coronary bypass graft procedures performed annually in the United States. Each of those procedures may include one or more graft vessels. Currently, each graft vessel must be hand sutured. As many as four or more grafts are placed in a procedure. Until recently, coronary artery bypass procedures have been performed with the patient on cardiopulmonary bypass whereby the heart is stopped with cardioplegia and the surgery performed on an exposed and still heart.

The previous applications disclosed means and methods for manipulating the heart during cardiac surgery whereby the heart can be located and oriented into the most advantageous position and orientation for beating heart surgery. Reference to those applications is made for a more complete discussion of the means and methods described.

Most particularly, the means and methods described in those applications include using a gross support to support the heart and a means for engaging a selected section of the heart to immobilize that selected section as a surgery target while permitting non-engaged sections of the heart to move in a manner whereby essentially unabated cardiac output is maintained while the heart is regionally immobilized.

The gross support means disclosed in the U.S. patent application Ser. No. 09/087,511 filed on May 29, 1998 includes a flexible cup that can move in a plurality of planes and which has a flexible rim for engaging the heart. The cup is releasably attached to the heart. One means for releasably attaching the cup to the heart includes suction applied by the cup to the heart. Suction is the best mode disclosed in the just-mentioned patent application.

As suction is readily available in most operating rooms, this is an effective means for releasably attaching the elements to the heart. However, this means can be improved.

Therefore, there is a need for a means and method for improving the releasable attachment between the elements of the heart manipulation system disclosed in the referenced patent applications and the heart.

The suction system disclosed in the referenced patent applications can also benefit by being backed up whereby the heart will remain in the desired position and orientation even if vacuum is lost or degraded.

Therefore, there is a need to provide a means for backing up the vacuum system used in the referenced patent applications to releasably attach the elements of the system to the heart.

Operation of the heart was discussed in the referenced patent applications and reference is made thereto for such disclosure so it will not be repeated here.

Recently, there has been interest in minimally invasive coronary bypass surgery. This is not surprising since a median sternotomy and a run on the cardiopulmonary bypass pump are not well tolerated by some patients, combined with the added cost of coronary bypass equipment and staff. The procedure results in considerable recovery time and is associated with a risk of death and major complication. While the ultimate goal is to provide bypass to all vessels by port access (like gallbladder surgery) and to eliminate the need for cardiopulmonary bypass, a more limited but reasonable option for the next number of years will be to perform bypass off pump with an incision (sternotomy or thoracotomy). A tool which could allow performance of multivessel off pump bypass would be most helpful.

Therefore, the referenced patent applications disclosed a heart retractor which will support the heart in position for minimally invasive coronary bypass surgery of coronary arteries, including the circumflex coronary artery, in a manner that will not damage the heart yet will provide easy access to the surgical target without requiring the heart to be stopped yet without unduly constraining the heart. These means and methods can also be improved by having additional means and methods for releasably attaching the elements of the systems to the heart during minimally invasive surgery.

OBJECTS OF THE INVENTION

It is a main object of the present invention to improve the performance of the system for manipulating a heart during cardiac surgery which was disclosed in the referenced patent applications.

It is another object of the present invention to improve the performance of the retractors disclosed in the parent disclosures.

It is another object of the present invention to improve the performance of the retractors disclosed in the parent disclosures by providing additional means for releasably attaching the elements of those systems to the heart.

It is a more specific object of the present invention to provide mechanical means for releasably attaching elements of a system for manipulating a heart during cardiac surgery.

It is a more specific object of the present invention to provide adhesive means for releasably attaching elements of a system for manipulating a heart during cardiac surgery.

SUMMARY OF THE INVENTION

These, and other, objects are achieved by providing mechanical and/or adhesive means for releasably attaching the elements of a system for manipulating a heart during cardiac surgery.

DETAILED DESCRIPTION OF THE PREFERRED EMBODIMENT OF THE INVENTION

The operation of a heart was discussed in the parent applications, and reference thereto is made for such discussion. Furthermore, the discussion of various elements of a heart manipulation system were also fully discussed in the parent applications.

Figure 9:
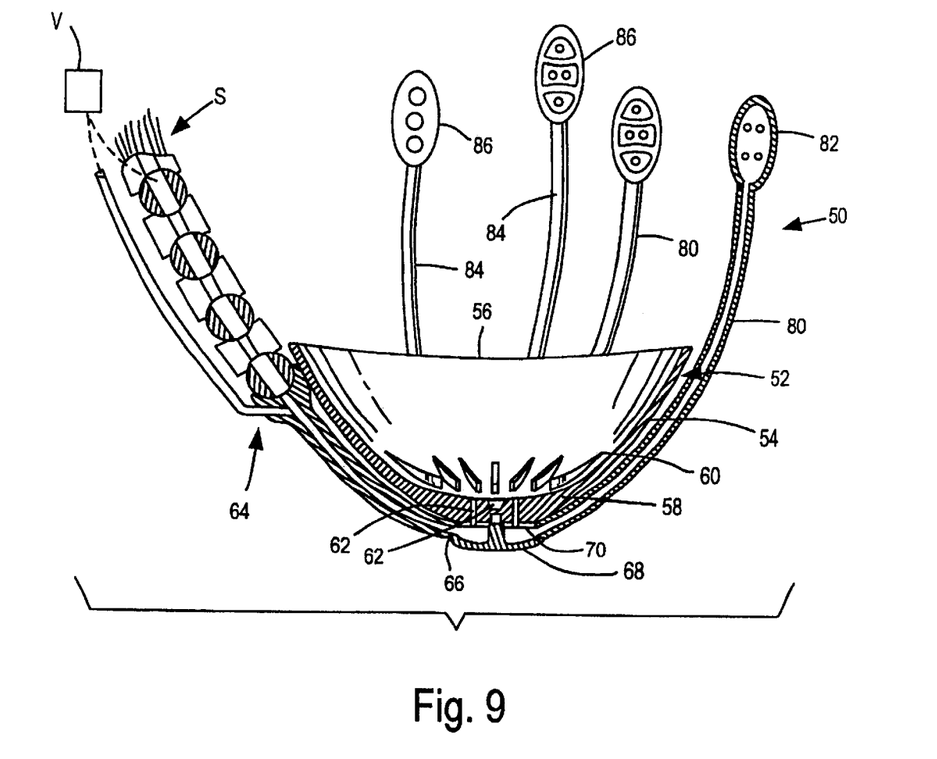
FIG. 9 is a side, cross-sectional view of a portion of a heart manipulation system disclosed in parent application Ser. No. 08/936,184.
Figure 10:
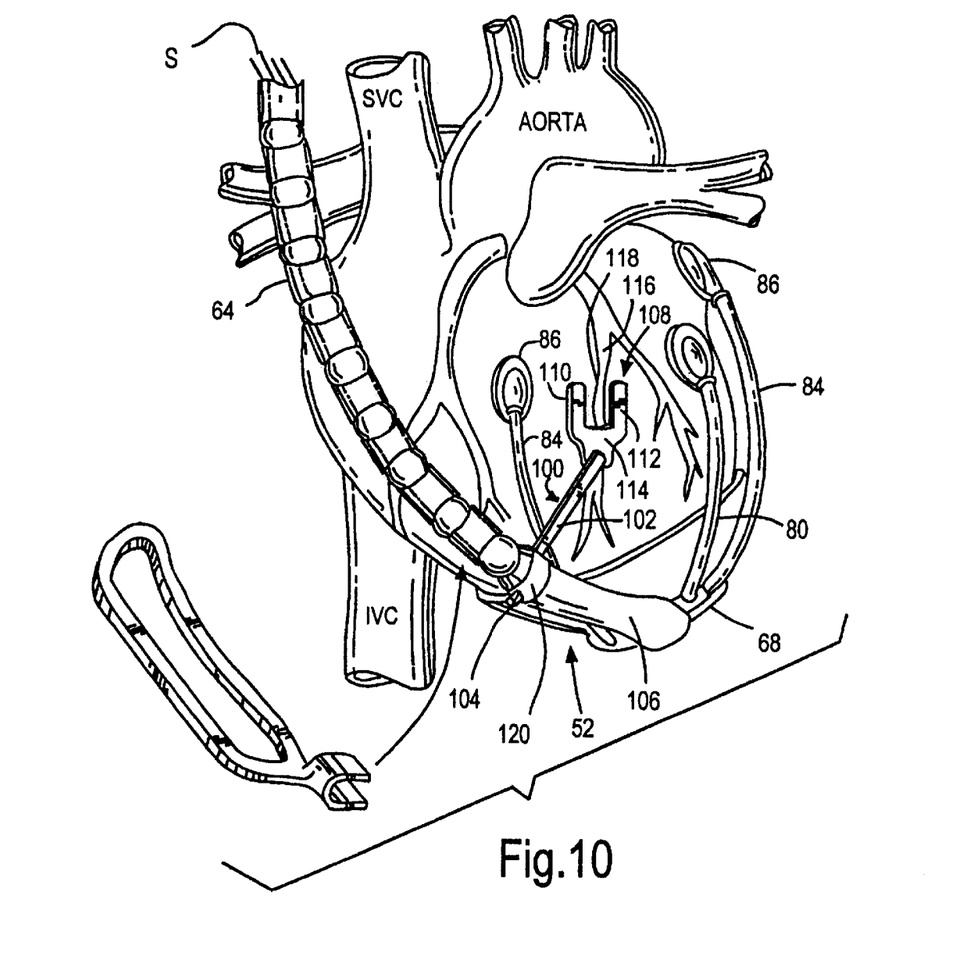
FIG. 10 is a perspective view of a portion of a heart manipulation system of FIG. 9, with a stabilizing element of a type disclosed in parent application Ser. No. 08/936,184.

FIGS. 9 and 10 correspond to FIGS. 3 and 5 of parent application Ser. No. 08/936,184, and show heart retractor 50 in detail. The retractor permits regional and specific immobilization of the heart while permitting essentially unabated cardiac output whereby all coronary arteries, including the circumflex coronary artery, to be bypassed and the heart maintained in an unnatural position and/or orientation. The retractor includes a gross support means 52 for engaging an apex portion (gross weight) of a heart to support the heart when the heart is lifted for surgery. Support means 52 includes a cup-shaped portion 54 having a top rim 56 and an apex 58 with ribs 60 defined adjacent to the apex to support the heart in the cup-shaped element. No limitation as to specific shape is intended for element 52. Vacuum ports 62 are defined through the cup-shaped element at apex 58 to be fluidically connected with a vacuum source for securing the heart in place in the cup-shaped element. A vacuum source V is fluidically connected to holes 62 via main support arm 64 which has one end thereof fixed to a stationary support S (see FIG. 10), such as the operating table, or a rib spreader, and the other end thereof attached to the cup-shaped element via fastener 66 attached to anchor 68. A manifold-like portion 70 of the cup-shaped element distributes the vacuum to the various ports, such as ports 62 to be applied to secure retractor 50 to the heart. An alternative form of the retractor includes a separate hose to transfer vacuum to the manifold 70. Ribs 60 keep heart fat from clogging the vacuum manifold section.

The retractor further includes a fine support means for immobilizing selected portions of the heart while permitting non-immobilized portions to move in a manner that continues heart operation. This fine support means includes a plurality of rigid arms 80 each being fixed at one end thereof to anchor 68 and having a heart-attaching element 82 thereon, such as at the outer end thereof. As used herein, the term "rigid" is a relative term and means that the arms are rigid enough whereby the force of the heart won't move them. But they can be adjustable such as being formed of a wire-wound gooseneck or soft metal which allows each arm to be individually shaped according to the needs of the attachment location. The heart-attaching elements can be suction attachment points, such as suction cups that are fluidically connected to manifold 70. Other means of attaching the elements to the heart can be used as well. Examples of other such elements include glue, sutures, clamps, shallow pins, pincers or the like, with attachment points being located on the arm as suitable. The rigid arms secure small or fine areas of the heart in place with respect to gross support element 52 while permitting the heart to move as required to continue unabated cardiac output. The retractor further includes a plurality of flexible support arms 84 each fixed at one end thereof to anchor 68 and having a heart-attaching element 86 on the outer end thereof. Elements 86 can be suction elements similar to the just-discussed elements 82. Flexible arms 84 can be adjusted to secure the heart in the most advantageous locations whereby the heart can continue to operate without undue restriction.

Referring to FIG. 10, it can be seen that the retractor includes a surgery target-immobilizing element 100 for immobilizing that exact location of the heart on which surgery is being performed. Element 100 includes a rigid arm 102 fixed at one end 104 to connecting arm 106 of stationary main arm 64 and having a U-shaped target-defining element 108 on the other end. Element 108 includes two legs 110 and 112 connected by a central section 114. As shown in FIG. 10, the target vein 116 being incised at 118 is located between legs 110 and 112. Element 108 is rigid as is arm 102 so target area 118 will be immobile even though the remainder of the heart adjacent to this area will be moving. However, only a small section of the heart will be immobilized and thus should not affect the overall operation of the heart during the operation. The target-immobilizing element can be moved anywhere it is needed by simply loosening clamp 120 and moving arm 102 as necessary.

FIGS. 11, 12, 13, 14, 15, and 16 correspond to FIGS. 7A, 8, 9, 24, 14B, and 14C of grandparent application Ser. No. 09/087.511. Grandparent application Ser. No. 09/087,511 discloses a heart manipulation system which utilizes a special suction cup to attach various elements thereof to the beating heart in a manner that permits the heart and the myocardium to move during heart operation without unduly affecting the attachment of the element to the heart. The suction cup applies suction to the heart surface from a source of suction. Such a suction cup disclosed in grandparent application Ser. No. 09/087,511 is suction cup 200 of FIG. 11 (of the present application), which is a suction cup that is most useful with non-flaccid tissue in which it is easier to make the suction cup conform to the tissue than to force the tissue to conform to the suction cup. Another suction cup disclosed in grandparent application Ser. No. 09/087,511 is most useful with flaccid tissue which is easier to force to conform to the shape of the suction cup.

Figure 11:
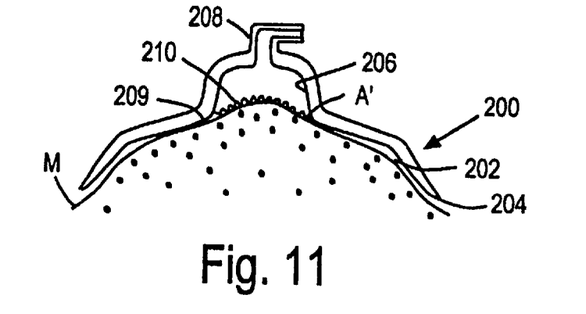
FIG. 11 is a cross-sectional view of a multipart suction cup disclosed in parent application Ser. No. 09/087,511.

Suction cup 200 shown in FIG. 11 includes a plurality of chambers and a means for preventing tissue from interfering with suction being applied thereto. Specifically, suction cup 200 is a multi-section suction cup which includes a first chamber 202 having a flexible rim 204 for engaging the tissue M of a heart, a second chamber 206 for fluidically connecting first chamber 202 with the source of suction via suction line 208. Second chamber 206 of the suction cup has a size that is different from the size of first chamber 202, and a shoulder 209 is formed at the connection between first and second chambers 202 and 206. A mesh grid element 210 is connected to the suction cup, preferably adjacent to shoulder 209 and spans first chamber 206. Flexible rim 204 is flexible in a plurality of planes to accommodate multiplanar movement of the surface of the beating heart without breaking contact between the surface of the heart and flexible rim 204.

As can be understood from FIG. 11, suction cup 200 will not break suction with tissue T even if the tissue is drawn into the suction cup and a large area of applied suction is maintained due to the large area A' of first chamber 206. Thus, suction cup 200 is able to adapt to movement of the heart and movement of the myocardium while maintaining a large suction force on the tissue. Since chamber 202 is large, rim 204 can be large and thus its flexibility can be increased.

Mesh grid element 210 functions to preserve suction pressure on the tissue even if the tissue is drawn into the suction cup. Thus, mesh grid element 210 has a first portion that can be engaged by the tissue, and a second portion that will remain open even when the first portion is engaged by tissue.

Figure 12:
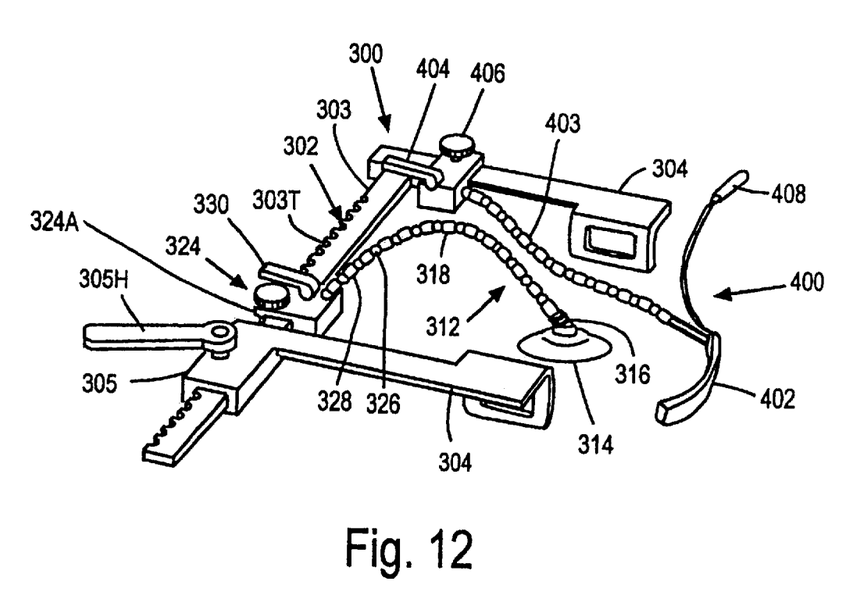
FIG. 12 is a perspective view of a system, disclosed in parent application Ser. No. 09/087,511, for manipulating a beating heart.

A heart manipulation system 300 for use in, cardiac surgery is broadly shown in FIG. 12 as comprising a frame 302 that can be located within the patient's thoracic cavity during beating heart surgery and which includes means for engaging the pericardial cavity of the patient for mounting said frame on the patient to move with the patient if the patient is moved or re-oriented during surgery.

Frame 302 includes a cross bar 303 that includes a multiplicity of teeth 303T thereon. Frame 302 further includes means for engaging the patient to support the frame in position in the patient. A preferred form of this means includes two sternal spacers 304 which set the depth of the frame into the chest cavity and keep the frame from twisting as the lungs inflate and which are connected on cross bar 303 by a ratchet-like mechanism 305 that has teeth which engage teeth 303T when the spacers are in the desired location. The frame is expanded inside the pericardial cavity with the cross bar. A handle 305H is operated to set the teeth of the mechanism 305 to teeth 303T. The frame can be either C-shaped or hoop shaped and can be secured to the patient or to an outside stable support. Other anchor means can be used.

A source of suction is located outside the patient and is used to attach various elements to the patient's heart. Most often, a source of vacuum is from the operating room source which provides approximately 100 to 180 mm of Hg vacuum.

Figure 13:
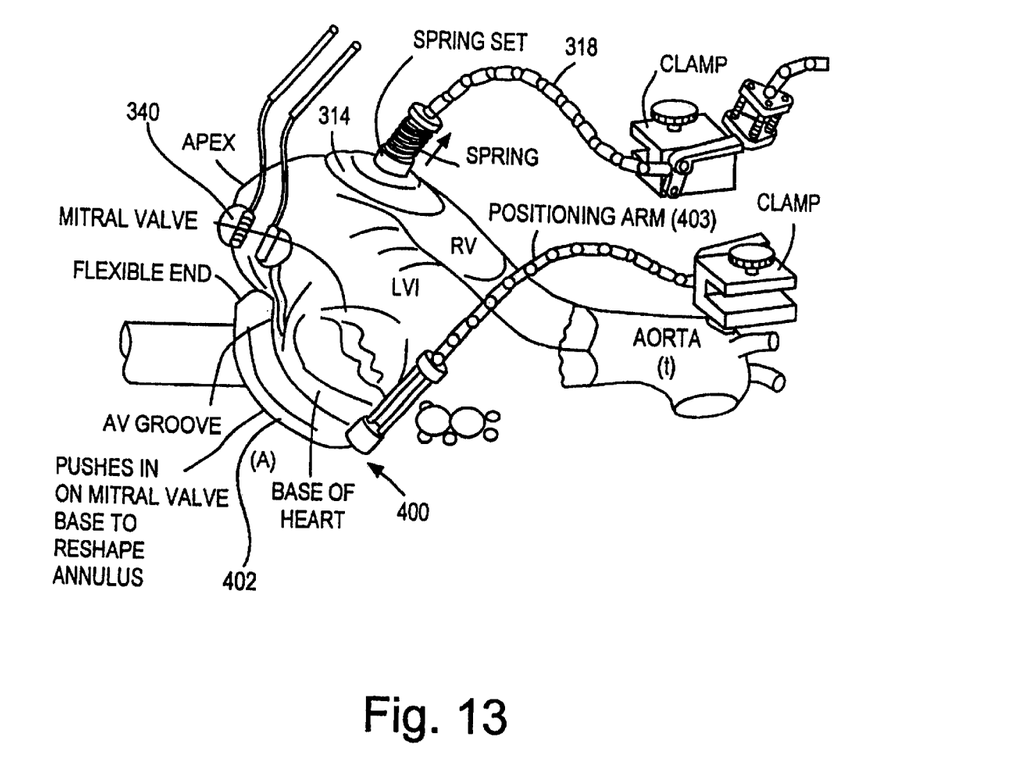
FIG. 13 is a perspective view of the system of FIG. 12 with surgery target immobilizing means, during cardiac surgery on a heart.
Figure 14:
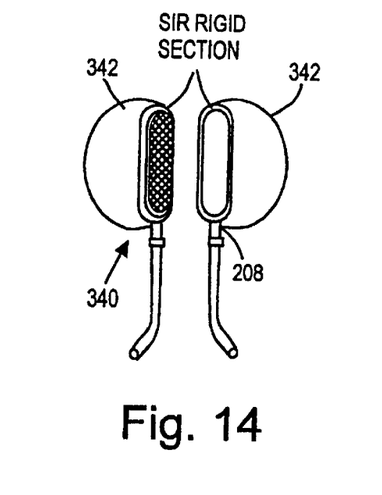
FIG. 14 is a perspective view of surgery target immobilizing means 340 of FIG. 13.

As shown in FIG. 12, system 300 includes a suspension head mechanism 312 movably mounted on frame 302 for lifting the heart. Mechanism 312 includes a head 314 which engages the heart and which is shown in FIG. 13 as being located near the apical region of the right ventricle to prevent collapse of the right ventricle during manipulation of the heart. As is also shown in FIG. 13, suspension head 314 at least partially overlies the right ventricle. Suspension head mechanism 312 includes a flexible means 316, such as a spring, for connecting flexible head 314 to arm 318 and for permitting multiplanar relative movement between the beating heart and arm means 318 mounting suspension head 314 on frame means 300. Suspension head 314 includes a suction cup such as disclosed above in FIG. 11 connected to the source of suction and which includes a flexible rim engaging the myocardium of the heart and being flexible in a plurality of planes so multiplanar movement of the myocardium during operation of the heart will be accommodated by the flexible rim whereby suction applied to the myocardium by the suction cup will not be broken by separation of the myocardium from the suction cup. The suction cup of head 314 includes means, such as the above-discussed mesh grid, for preventing heart tissue from interfering with suction being applied to the myocardium via head 314.

Arm 318 is flexible in one condition as discussed in the parent disclosure, and is made rigid by manipulation of control and anchor element 324. Anchor element 324 includes a base 324A which is movably mounted on cross bar 303 and has internal teeth that engage teeth 303T. and a lever system for locking the internal teeth of element 324 to teeth 303T when desired. A further lever-operated mechanism locks corresponding elements in arm 318 whereby arm 318 is rendered rigid. Arm 318 includes a flexible central line extending from head 314, through flexible element 316 to anchor element 324 and a plurality of relatively movable sections, such as balls 326 interposed between links 328, on the central line. A lever 330 is connected to the central line and when the lever is operated, the elements 326 and 328 are forced together to render the arm rigid. In this manner, the suspension head 314 can be easily maneuvered on a flexible arm into the desired position and then locked into that position by rendering arm 318 rigid. Flexible means 316 permits multiplanar movement of suspension head 314 even after arm 318 is made rigid whereby movement of a beating heart is accommodated by suspension head mechanism 312. When suction is applied to the heart via head 314 the heart will be suspended and can be lifted into the desired position and orientation for cardiac surgery without interrupting cardiac output. The combination of the suction cup, the flexible/rigid arm, the flexible means and the location of the head on the heart effect this result. Various forms of head 314 can be used.

With the heart supported by suspension means 312, the cardiac surgery can be completed if desired. As will be discussed below, however, additional support can be provided. A surgery target immobilizer can be used to locally immobilize the heart while permitting the non-engaged portions of the heart to continue to operate so as to maintain cardiac output essentially unabated. Means 340 (shown in FIGS. 13 and 14) is a means for locally engaging a selected section of the heart and locally immobilizing the heart adjacent to a surgery target so the heart is supported by the suspension head mechanism and can receive further support from the surgery target immobilizing means and can thus be free to operate during surgery while it is also locally immobilized at the surgery target with non-engaged sections of the heart free to move in a manner whereby essentially unabated cardiac output is maintained while the heart is locally immobilized. Each surgery target immobilizing means 340 includes a flexible section 342, such as suction cup, on a rigid element SIR. The suction cups attached to each rigid element are connected by suction line 208 to the source of suction and each includes a flexible rim engaging the myocardium of the heart and being flexible in a plurality of planes so multiplanar movement of the myocardium during operation of the heart will be accommodated by the flexible rim of the surgery-target immobilizing means whereby suction applied to the myocardium by the suction cup of the surgery target immobilizing means will not be broken by separation of the myocardium, from the suction cup of the surgery target immobilizing means. Suction cups of the surgery target immobilizing means each include means for preventing heart tissue from interfering with suction being applied to the myocardium via said suction cup of the surgery target immobilizing means.

In some circumstances, two point support is preferred when performing cardiac surgery. Accordingly, manipulation system 300 provides a gross support means 400 movably mounted on frame 302 for engaging the heart to support the heart when the heart is oriented for surgery and which can be located at the base of the heart and which cradles the myocardium of the left ventricle along the arterialventricular groove TAVX Gross support means 400 is shown in FIGS. 12, 13, 15, and 16. As broadly shown in FIG. 12, gross support means 400 includes a head 402 that is engaged with the heart and which is movably connected to frame 302 by an arm mechanism 403 similar to arm 318 to be flexible and movable with respect to the heart and with respect to frame 302 when desired, and then rendered rigid by operation of a lever 404 of an anchor mechanism 406 that can be located on cross bar 303 or on one of the sternum retractors 304. Operation of the flexible arm 403 is identical to that of arm 318 and thus will not be again discussed.

Gross support means 400 supports the mitral valve annulus to maintain competent mitral valve function and head 402 is placed beneath an infolded section of myocardium. Gross support means 400 includes a handle 408 which is attached to head 402 and which extends outside of the patient during surgery for adjusting the location of gross support means head 402.

Figure 15:
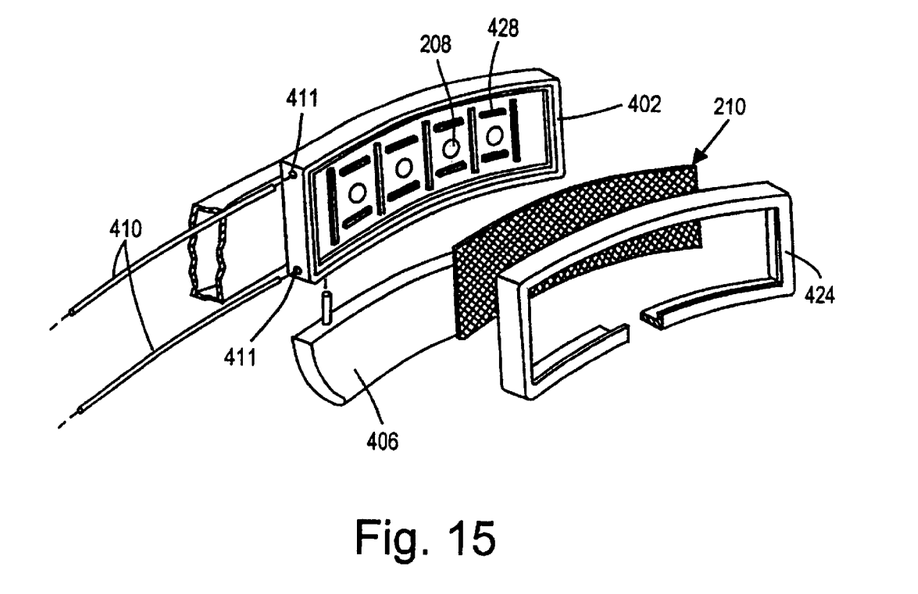
FIG. 15 is an exploded perspective view of a portion of gross support means 402 of the system of FIG. 12.
Figure 16:
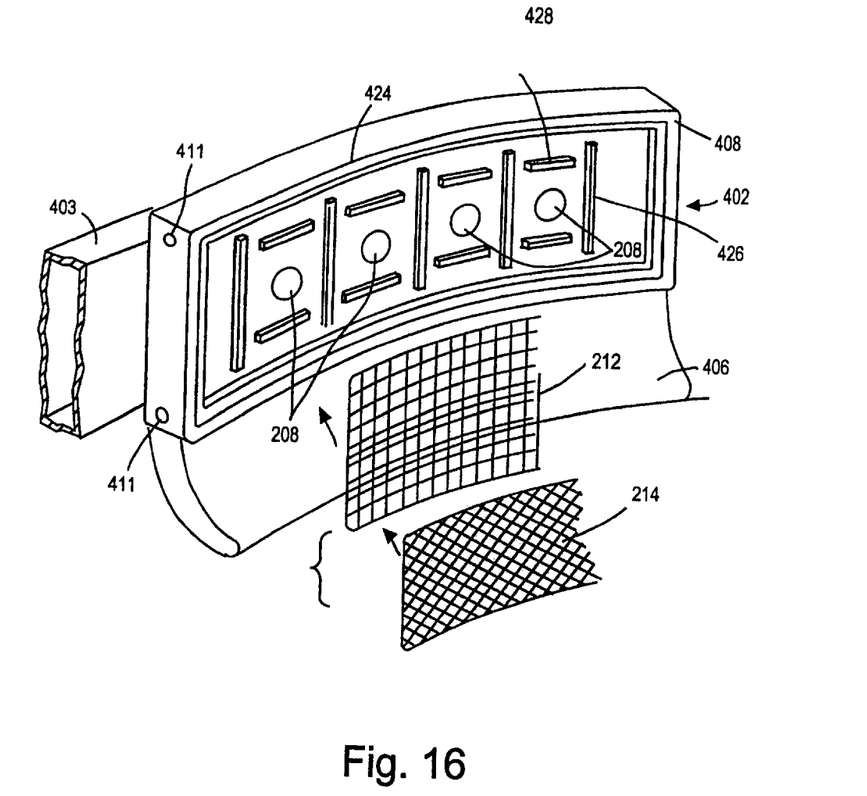
FIG. 16 is another exploded view of gross support means 402 of the system of FIG. 12.

Head 402 is shown in FIGS. 15 and 16 as including a rigid support section 406 connected to a flexible section 408 having malleable rod means 410 received in bores 411 defined in head 402 for retaining a configuration that has been set for head 402 and for connecting head 402 to the arm 403 for mounting gross support means 400 on frame 302. Head 402 can include a plurality of sections which are movable relative to each other and means for maintaining those sections in a selected relative orientation. In this manner, head 402 can be shaped to best support the heart and can be adjusted to meet the needs of an individual heart. As head 314 is also adaptable to the size and shape of an individual heart, the two-point support of system 300 can be adjusted and customized to fit the exact needs of each individual heart.

As shown in FIGS. 15 and 16, head 402 includes means for applying suction from the source of suction to the heart. This means includes a mesh grid means 210 attached to head 402 and spanning a first chamber above a suction applying manifold that is fluidically connected to the source of suction by suction line 208 for preventing heart tissue from interfering with suction applied by suspension head 402 to the heart. Frame 424 maintains mesh grid means 210 (which comprises first portion 212 and second portion 214) in place on head 402, and ribs, such as rib 426 and 428 can be used to maintain the desired position of mesh grid element 210 with respect to suction holes 208.

Using the system 300, a method of performing heart surgery comprises steps of placing frame 300 in the patient, slightly infolding the left atrium of a heart adjacent to the base of the heart, engaging the heart under the edge of the myocardium at the base of the heart with gross support means 400 then using handle 408 tilting and lifting the heart. The heart is engaged near the apex of the heart with suspension head 314 to lift the heart. Such engagement prevents right ventricle collapse. This provides two point support if desired. However, the suspension means alone may be sufficient in some cases to move the heart as necessary. The method can further include a step of using surgery target immobilizing means 340 shown in FIG. 14 to apply suction to the heart adjacent to the selected surgical target for engaging that selected section of the heart and immobilizing that selected section as a surgery target while permitting on-engaged sections of the heart to move and permitting essentially unabated cardiac output to be maintained while the heart is regionally immobilized.

Alternative forms of the frame 300 can be used, provided the frame is located to move with the patient.

The improvement in the heart manipulation system which is the subject of the present invention utilizes either mechanical or adhesive means to releasably attach an element of a heart manipulation system to the heart. These means can be used in place of or in addition to the means disclosed in the parent applications.

Figure 1:
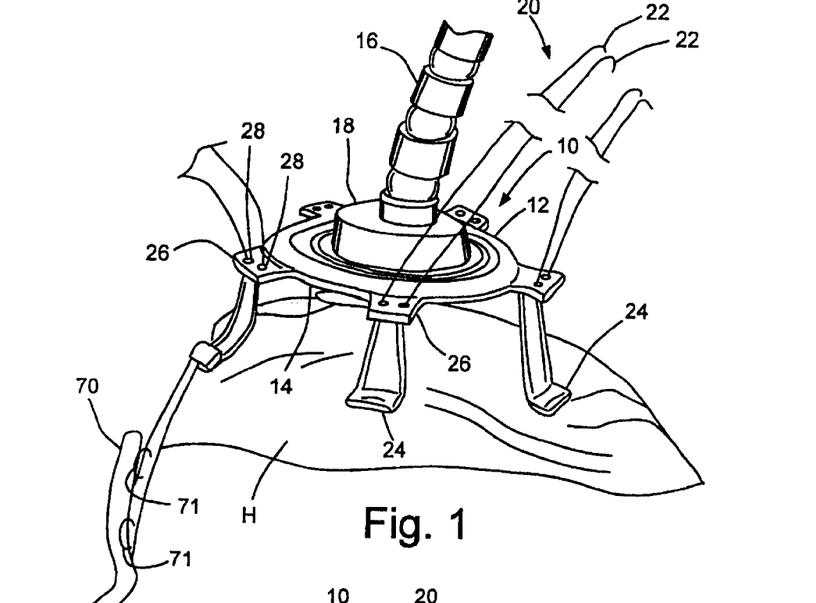
FIG. 1 illustrates a suspension head mechanism such as disclosed in parent application Ser. No. 09/087,511 for lifting the heart.

As shown in FIG. 1, a special cup 10 is used to attach various elements of the heart manipulation system to the beating heart H in a manner that permits the heart and the myocardium to move during heart operation without unduly affecting the attachment of the element to the heart. The cup 10 can be adapted to apply suction to the heart, but need not and can be designed to have several degrees of freedom whereby the heart can move without undue restriction from cup 10. Specifically, cup 10 has a flexible wall 12 and a flexible rim 14 and is attached to an arm 16 at an apex portion 18 of the cup. The flexible wall permits the cup to move in a plurality of planes so the heart can move relative to arm 16.

The means for releasably attaching cup 10 to the heart can include mechanical means. As used herein, the term "mechanical means" includes sutures, staples and other such mechanical elements and fasteners as opposed to suction and chemical means.

One form of mechanical means for releasably attaching elements of the heart manipulation system to the heart includes sutures 20. Sutures 20 include needles 22 which are threaded through the heart manipulation system element, such as cup 10, and then through the heart tissue, and then back through the heart tissue and back through the system element and out of the patient. Sutures 20 can also include elements, such as pledgets 24 for holding the suture in place on the heart and for spreading out the force applied by each suture to the heart tissue. The sutures can be set in any manner known to those skilled in the art. Once set, the sutures are tied off and then serve as a means for attaching the system element to the heart. The sutures are cut when the element is to be released from the heart.

As shown in FIG. 1, the element, such as cup 10, can include extensions, such as extension 26, having suture-accommodating holes 28 defined therethrough. However, the element need not include the extensions, and the holes 28 can be defined in the element itself or the sutures can be drawn through the element without the need of such holes 28 without departing from the scope of the present disclosure.

In one embodiment, the invention is a heart manipulation system (including the elements shown in FIG. 1) for use in cardiac surgery, the system comprising: a frame (e.g., a frame such as frame 302 of FIG. 12) configured to be located inside a patient during beating heart surgery and which includes means for engaging the pericardial cavity of the patient for mounting said frame on the patient to move with the patient if the patient is moved or re-oriented during surgery; a suspension head (e.g., cup 10) movably mounted on said frame for lifting the heart and which is configured to be positioned near the apical region of the right ventricle to prevent collapse of the right ventricle during manipulation of the heart and at least partially overlying the right ventricle and which includes a flexible means (e.g., flexible wall 12 of FIG. 1 or means 316 of FIG. 12) for permitting multiplanar relative movement between the beating heart and means mounting the suspension head on the frame means, said suspension head including a flexible rim engaging the myocardium of the heart and being flexible in a plurality of planes so multiplanar movement of the myocardium during operation of the heart will be accommodated by the flexible rim; means for releasably attaching the suspension head to the heart (e.g., sutures 20 of FIG. 1); a gross support means 70 (shown in FIG. 1) movably mounted on the frame for engaging the heart to support the heart when the heart is oriented for surgery and which is configured to be positioned at the base of the heart to cradle the myocardium of the left ventricle along the arterialventricular groove: and means for releasably attaching the gross support means to the heart (means 71 shown in FIG. 1).

Figures 2, 3:
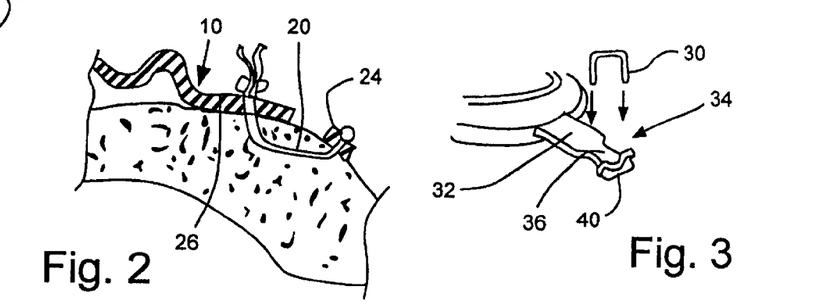
FIG. 2 illustrates one mechanical means for releasably attaching the suspension head to the heart as including a suture.
FIG. 3 illustrates one mechanical means for releasably attaching the suspension head to the heart as including a staple.

While sutures 20 are shown in FIGS. 1 and 2 as extending through extensions 26 of cup 10, these sutures could be sewn through the element itself without departing from the scope of the present invention. In fact, the sutures need not be located near the perimeter of the element, but could be placed in any suitable location on the element without departing from the scope of the present invention. The sutures can be manipulated in any suitable manner and can take the form of any suture known to those skilled in the art without departing from the scope of the present disclosure. Those skilled in the art will understand what type of suture works best in any given application based on their own knowledge and the teaching of the present invention and the present disclosure. Accordingly, the term "suture" is intended to cover any suture known to those skilled in the art that will work in the application disclosed herein.

Figure 4:
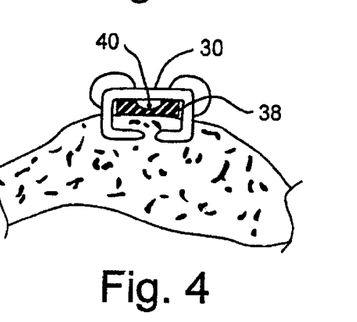
FIG. 4 is another view of the staple shown in FIG. 3 in the formed condition.
Figure 5:
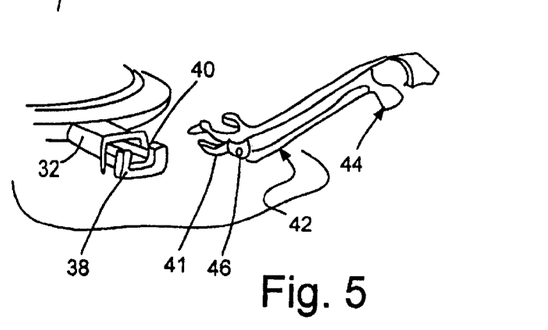
FIG. 5 illustrates a staple-removing element.

Yet another form of mechanical means for releasably attaching an element of the heart manipulation system to the heart is shown in FIGS. 3 and 4 as including a staple 30. Staple 30 is set and formed according to known procedures from the unformed condition shown in FIG. 3 to the formed configuration shown in FIG. 4. Staples, such as those used to close skin can also be used and still be within the teaching of this invention. An extension 32 is included on the heart manipulation system element, such as cup 10, and has a distal end 34 with a neck 36 defined therein. A tab 38 is located on the distal end and includes a groove 40 that permits a portion 41 of a staple removing tool, such as tool 42 shown in FIG. 5, to be inserted beneath the staple for removing that staple from the formed configuration shown in FIG. 4. Once the staples are removed, the element can be released from attachment to the heart. Portion 41 is manipulated by handle 44 via pivot 46 to unform the staple to release the staple from the heart.

Figure 6:
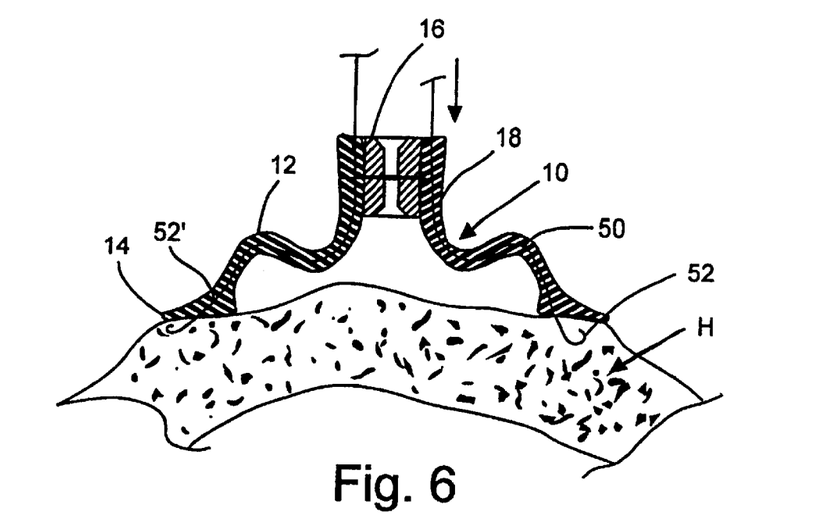
FIG. 6 illustrates one mechanical means for releasably attaching the suspension head to the heart as including a suture.
Figure 7:
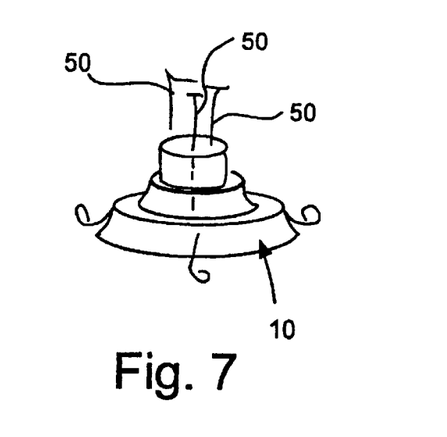
FIG. 7 is another form of the suture mechanical attaching means shown in FIG. 6.

Yet another form of mechanical means is illustrated in FIGS. 6 and 7 as a plurality of anchor wires 50 located inside the element being releasably attached to heart H. Each anchor wire 50 includes a curled, pre-shaped end 52 which curls up inside the heart tissue once the wire is inserted into the tissue to fasten the element to the heart. The anchor wires extend inside the element from apex 18 to and out of rim 14 and the curled bias thereof is overcome by the inside surface of the element as indicated at end 52' shown in FIG. 6. The wire curls as it exits the element and enters the heart tissue. A plurality of wires can be used as indicated in FIG. 7, and the wires can be used in conjunction with, or in place of, suction and/or other mechanical means, such as the sutures and/or staples disclosed hereinabove.

Figure 8:
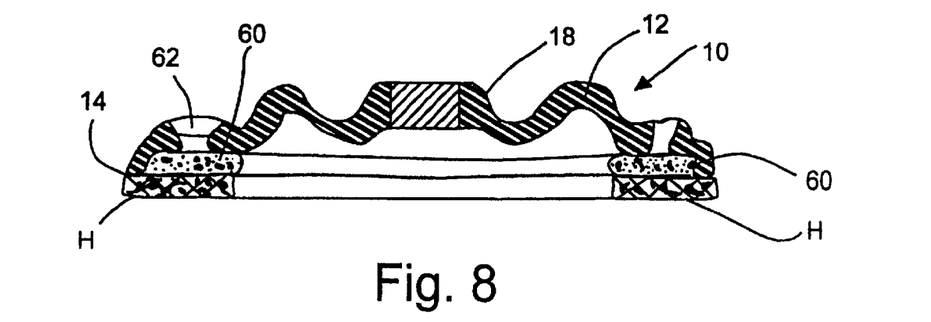
FIG. 8 illustrates an adhesive means for attaching an element of the heart manipulation system to the heart.

An adhesive means can also be used to releasably attach the heart manipulation system element to the heart. As shown in FIG. 8, surgical adhesive 60 can be placed on the element near rim 14 to releasably attach the element to heart H. A wick 62 can be included in the element to ensure the delivery of bonding activators or de-bondingagents directly to the adhesive layer. Solvent can be applied to the adhesive via wick 62 to release the adhesive from the heart as will occur to those skilled in the art based on the teaching of the present disclosure. Any suitable surgical adhesive can be used and those skilled in the art will understand what adhesive is best based on the teaching of the present disclosure. In addition, heat or light or moisture sensitive adhesives could be used to releasably attach elements of the heart manipulation system to the heart without departing from the scope of the present disclosure. The particular adhesive forms no part of the present invention and thus will not be discussed.

As is the case above, the adhesive can be used in conjunction with or in place of the suction and/or the mechanical means for releasably attaching the element to the heart.

It is understood that while certain forms of the present invention have been illustrated and described herein, it is not to be limited to the specific forms or arrangements of parts described and shown. For example, tissue-gripping needles on a pad can be used to attach the elements of the heart manipulation system to the heart, such tissue-gripping needles would be self-contained and quickly deployed. These needles would work in the manner of a skin stapler but would be more convenient since they could be deployed by a mechanism on the attachment element. Such needles can be anchored to the element being attached to the heart, and released using tools similar to those used to remove small suture needles in other applications or have integrated deployment or retraction means. The needles need not be formed with a forming device but can also be of a pre-formed configuration, such as a helix, or the like and can be self-tapped into the heart. The heart attachment system is not dependent on suction alone and, as can be understood from the foregoing teaching, can include various other means in addition to, or instead of, suction. Combinations of the various mechanical and adhesive and suction means can be used as will be understood from the teaching of this disclosure.

What is claimed is:

1. A manipulation system for cardiac surgery comprising:
   a suspension head having a periphery;
   extensions extending outward from said periphery of said suspension head; and
   releasable attachment means for releasably attaching said extensions to the heart.

2. The manipulation system of claim 1, wherein said suspension head comprises a cup.

3. The manipulation system of claim 2, wherein said cup comprises a flexible wall.

4. The manipulation system of claim 3, wherein said cup further comprises a flexible rim.

5. The manipulation system of claim 2, wherein said cup comprises a flexible rim.

6. The manipulation system of claim 2, wherein said cup comprises an apex, said apex being attached to an arm.

7. A manipulation system for cardiac surgery comprising:
   a suspension head comprising a cup having a flexible wall and a flexible rim; and
   releasable attachment means, extending outside a periphery of said suspension head, for releasably attaching said cup to the heart.

8. The manipulation system of claim 7, wherein said cup further comprises an apex, said apex being attached to an arm.

9. A manipulation system for cardiac surgery comprising:
   a suspension head adapted to attach to a surface of the heart by suction; and
   releasable attachment means comprising at least one mechanical or chemical means for releasably attaching said suspension head to the heart, wherein said suspension head is configured to exert lifting force on the heart, and wherein said releasable attachment means further assure that said suspension head does not become unexpectedly detached from the heart when attached to the heart by the releasable attachment means.

* * * * *